US012637357B2

(12) United States Patent
Walter et al.

(10) Patent No.: US 12,637,357 B2
(45) Date of Patent: May 26, 2026

(54) PROCESS AND PLANT FOR PRODUCING METHANOL AND AMMONIA

(71) Applicant: L'Air Liquide, Société Anonyme pour l'Etude et l'Exploitation des Procédés Georges Claude, Paris (FR)

(72) Inventors: Stefan Walter, Griesheim (DE); Stephan Haase, Steinbach (DE); Manon Cortale, Vincennes (FR); Sophia Schmidt, Frankfurt am Main (DE)

(73) Assignee: L'Air Liquide, Societe Anonyme Pour l'Etude et l'Exploitation des Procedes, Georges Claude Paris (FR)

( * ) Notice: Subject to any disclaimer, the term of this patent is extended or adjusted under 35 U.S.C. 154(b) by 890 days.

(21) Appl. No.: 17/709,632

(22) Filed: Mar. 31, 2022

(65) Prior Publication Data

US 2022/0315434 A1 Oct. 6, 2022

(30) Foreign Application Priority Data

Mar. 31, 2021 (EP) .................................... 21020173

(51) Int. Cl.
*C01C 1/04* (2006.01)
*B01D 53/14* (2006.01)
(Continued)

(52) U.S. Cl.
CPC ........ *C01C 1/0488* (2013.01); *B01D 53/1475* (2013.01); *B01J 19/2465* (2013.01);
(Continued)

(58) Field of Classification Search
USPC .......................................................... 423/700
See application file for complete search history.

(56) References Cited

U.S. PATENT DOCUMENTS

| | | | |
|---|---|---|---|
| 5,827,901 | A | 10/1998 | Konig et al. |
| 2004/0028595 | A1 | 2/2004 | Davey et al. |
| 2007/0299144 | A1 | 12/2007 | Davey et al. |

FOREIGN PATENT DOCUMENTS

| | | |
|---|---|---|
| EP | 0 790 226 | 8/1997 |
| EP | 2 196 448 | 6/2010 |

(Continued)

OTHER PUBLICATIONS

WO 2005/095313 A1—English language translation (Year: 2005).*

(Continued)

*Primary Examiner* — Anthony J Zimmer
(74) *Attorney, Agent, or Firm* — Allen E. White

(57) ABSTRACT

What is proposed is a process and a plant for parallel production of methanol and ammonia by heterogeneously catalyzed reaction of hydrogen and carbon oxides on the one hand and hydrogen and nitrogen on the other hand. This includes producing a raw synthesis gas stream and dividing it into two portions. A first raw synthesis gas substream is used as input for a methanol synthesis to obtain raw methanol and a methanol synthesis purge stream. A second raw synthesis gas substream is subjected to a CO conversion, a carbon dioxide separation and a liquid nitrogen scrubbing and then sent to an ammonia synthesis. According to the invention at least a portion of the methanol synthesis purge stream is sent to the ammonia synthesis and at least one substream obtained from the second raw synthesis gas substream is passed to the methanol synthesis.

6 Claims, 1 Drawing Sheet

(51) Int. Cl.

| | |
|---|---|
| ***B01J 19/24*** | (2006.01) |
| ***C01B 3/36*** | (2026.01) |
| ***C01B 3/382*** | (2026.01) |
| ***C01B 32/40*** | (2017.01) |
| ***C07C 29/152*** | (2006.01) |

(52) U.S. Cl.

CPC ................ *C01B 3/36* (2013.01); *C01B 3/382* (2013.01); *C01B 32/40* (2017.08); *C07C 29/152* (2013.01); *B01D 2252/2021* (2013.01); *B01J 2219/00186* (2013.01); *C01B 2203/0233* (2013.01); *C01B 2203/0244* (2013.01); *C01B 2203/025* (2013.01); *C01B 2203/0415* (2013.01); *C01B 2203/042* (2013.01); *C01B 2203/061* (2013.01); *C01B 2203/068* (2013.01); *C01B 2203/0811* (2013.01); *C01B 2203/1241* (2013.01); *C01B 2203/148* (2013.01)

(56) References Cited

FOREIGN PATENT DOCUMENTS

| | | | | |
|---|---|---|---|---|
| EP | 2196448 B1 * | 6/2010 | ............ | B01J 8/0411 |
| WO | WO 02 38499 | 5/2002 | | |
| WO | WO 2005 095313 | 10/2005 | | |
| WO | WO-2005095313 A1 * | 10/2005 | ............ | C01B 3/025 |

OTHER PUBLICATIONS

Haring, H.-W., Industrial Gases Processing, Wiley-VCH Verlag Gmbh & Co KGaA, 2008, Weinheim, Germany, p. 156.

Ullmann's Encyclopedia of Industrial Chemistry, Sixth Edition, 1998 Electronic Release, Ammonia, Production, 73 pages.

Ullmann's Encyclopedia of Industrial Chemistry, Sixth Edition, 1998 Electronic Release, Methanol, Process Technology, 6 pages.

European Search Report for corresponding EP 21020173, Sep. 14, 2021.

* cited by examiner

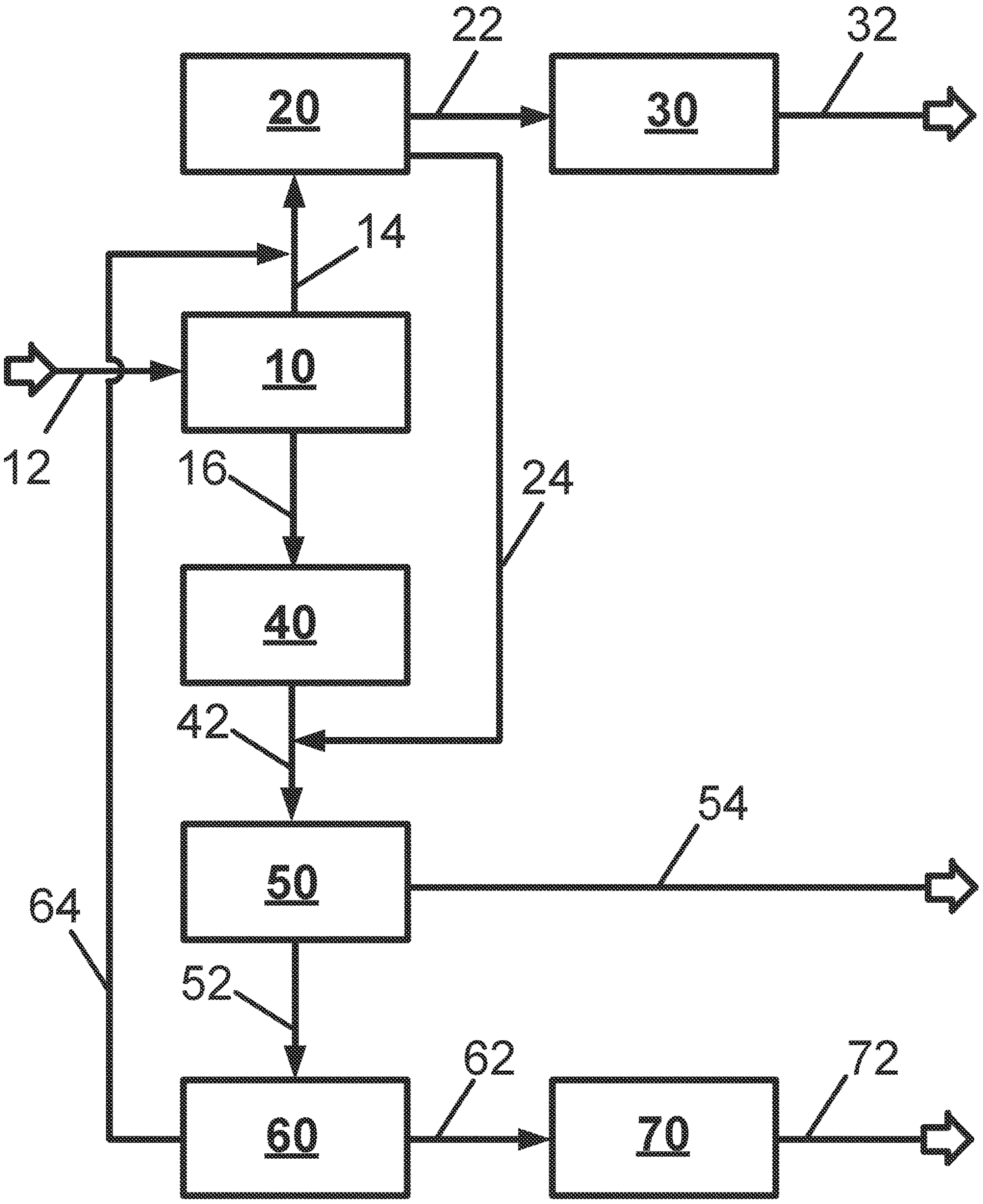
22
32
20
30
14
10
12
16
24
40
42
54
50
64
52
62
72
60
70

PROCESS AND PLANT FOR PRODUCING METHANOL AND AMMONIA

CROSS REFERENCE TO RELATED APPLICATIONS

This application claims the benefit of priority under 35 U.S.C. § 119(a) and (b) to European Patent Application No. EP 21020173.7, filed Mar. 31, 2021, the entire contents of which are incorporated herein by reference.

BACKGROUND

Field of the Invention

The invention relates to a process for parallel production of methanol and ammonia by heterogeneously catalyzed reaction of hydrogen and carbon oxides on the one hand and hydrogen and nitrogen on the other hand in corresponding synthesis reactors known per se, wherein the focus of the invention is on the production, conditioning and optimized material utilization of the synthesis gas required therefor. The invention further relates to a plant for performing such a production process.

Prior Art

Processes for industrial production of methanol and ammonia by heterogeneously catalyzed conversion of synthesis gas or the hydrogen present therein in suitable synthesis reactors have long been known in the art. Synthesis gases are gas mixtures containing hydrogen and carbon oxides which are used in various synthesis reactions.

Both substances constitute important indispensable feedstock chemicals of the chemical industry for further processing into end products. Ullmann's Encyclopedia of Industrial Chemistry, Sixth Edition, 1998 Electronic Release, chapter "Methanol", subchapter 5 "Process Technology" and chapter "Ammonia", subchapter 4 "Production" describes various basic processes for producing the recited substances.

A modern two-stage process for producing methanol is disclosed in European patent specification EP 0 790 226 B1 for example. The methanol is produced in a circular process wherein a mixture of fresh and partly reacted synthesis gas is supplied initially to a water-cooled reactor (WCR) and then to a gas-cooled reactor (GCR), in each of which the synthesis gas is converted over a copper-based fixed-bed catalyst to afford methanol. The methanol produced in the process is separated from the synthesis gas to be recycled which is then passed through the gas-cooled reactor in countercurrent as coolant and preheated to a temperature of 220° C. to 280° C. before it is introduced into the first synthesis reactor. A portion of the synthesis gas to be recycled is removed from the process as a purge stream to prevent inert components from accumulating in the synthesis circuit.

Unconverted methane from synthesis gas production is considered an inert component in the context of methanol synthesis and also ammonia synthesis since this compound does not undergo further conversion under the conditions of methanol or ammonia synthesis. The same applies to argon which passes into synthesis gas production via feed streams.

A current process for ammonia synthesis is described for example in patent publication WO 2002/038499 A1. Compared to the synthesis gas used for methanol synthesis it is important in the case of synthesis gas for ammonia synthesis to completely eliminate the proportion of carbon oxides, so that hydrogen passes into the ammonia synthesis as the sole remaining synthesis gas constituent. This is effected initially through conversion of the carbon monoxide present in the synthesis gas (CO conversion), a subsequent carbon dioxide removal by means of a sorption process and finally by means of cryogenic gas fractionation.

There are different processes for producing synthesis gas comprising hydrogen and carbon oxides as input gas for methanol synthesis and ammonia synthesis, for example steam reforming, autothermal reforming (ATR), combinations thereof (so-called combined reforming) and noncatalytic partial oxidation (POX). Technical details of these processes are known in the art and are comprehensively described in, for example, Ullmann's Encyclopedia of Industrial Chemistry, Sixth Edition, 1998 Electronic Release, keyword "Gas Production".

A particularly often realized variant of steam reforming is the steam reforming of natural gas as input gas. Due to the high methane content of natural gas this is also referred to as steam methane reforming (SMR).

A further variant of steam reforming does not comprise heating the catalyst-filled reactor tubes, also known as cracking tubes, by thermal radiation using burner flames but rather comprises using hot flue gases or hot synthesis gas from a downstream reforming stage, for example from an ATR, to heat the reactor tubes in order to transfer thereto the energy required for the endothermic steam cracking. The heat transfer proceeds largely by convective means and the corresponding reformer type is known as a gas heated reformer (GHR).

Starting materials for the abovementioned processes for synthesis gas production include hydrocarbons such as natural gas, comprising its main component methane or naphtha. The recited processes afford different ratios of the product components carbon monoxide (CO) and hydrogen ($H_2$) as is apparent from the following reaction equations:

$$2\ CH_4 + O_2 = 2\ CO + 4\ H_2$$

$$2\ CH_2 + 1/2\ O_2 + H_2O = 2\ CO + 5\ H_2$$

$$2\ CH_4 + 2\ H_2O = 2\ CO + 6\ H_2$$

(partial oxidation)
(autothermal reforming)
(pure steam reforming)

Since partial oxidation or autothermal reforming is operated with an excess of hydrocarbon/deficiency of oxygen to inhibit the total oxidation of the hydrocarbons to carbon dioxide a synthesis gas is often obtained which has a hydrogen deficit having regard to its use as input gas for methanol synthesis. This necessitates according to the following reaction equation $$2\ H_2 + CO = CH_3OH$$

an $H_2/CO$ ratio of at least 2 and under practical synthesis conditions often slightly greater than 2, for example 2.1. This ratio is typically formulated as the stoichiometry number SN of the methanol synthesis and takes into account that carbon dioxide too reacts to afford methanol.

$$SN = ([H_2] - [CO_2]) / ([CO] + [CO_2]) \geq 2$$

By contrast, synthesis gases obtained by partial oxidation or autothermal reforming often have a stoichiometry number of ≤1.9, occasionally even ≤1.7 auf. Accordingly, none of the reforming/partial oxidation processes in themselves afford a synthesis gas product having the stoichiometric $H_2/CO$ ratio of 2 or only a slight hydrogen excess desired for the methanol synthesis.

It is moreover necessary, having regard to the ammonia synthesis to be performed in parallel, to separate carbon oxides in the proportion of synthesis gas assigned as the feed therefor and to maximize the proportion of hydrogen. This is typically effected by means of the CO conversion reaction, also known as the water gas shift reaction (WGS) or CO shift reaction, according to the reaction equation $$CO + H_2O = CO_2 + H_2$$

Addition of steam causes the CO to react to afford $CO_2$ and $H_2$. Depending on the employed reaction temperature, the reaction is referred to as a high temperature shift (HTS), medium temperature shift (MTS) or low temperature shift (LTS).

The further workup of the produced raw synthesis gas usually also comprises a sorption process for separating further unwanted concomitants, for example by physical or chemical absorption or gas scrubbing. Such processes thus allow unwanted constituents, in particular carbon dioxide ($CO_2$), to be safely removed down to trace amounts from the desired main synthesis gas constituents hydrogen and carbon monoxide. A known and often employed process is the Rectisol process which comprises a scrubbing of the raw synthesis gas with cryogenic methanol as the absorbent and is likewise described in principle in the abovementioned document.

Cryogenic gas fractionation (so-called coldbox) may also be used to remove traces of higher hydrocarbons or of carbon monoxide. This employs mainly liquid methane or liquid nitrogen to absorb higher boiling gases such as carbon monoxide. Workup of the hydrogen required for the ammonia synthesis is typically effected by performing a liquid nitrogen scrubbing which advantageously affords a hydrogen/nitrogen mixture having the ratio ideal for ammonia synthesis of 3 mol/mol. The thus obtained offgas stream may be used as fuel gas or alternatively separated into a methane-rich gas stream and into a further carbon monoxide- and hydrogen-comprising gas stream by means of further cryogenic gas fractionation if desired or required.

A process for combined synthesis of ammonia and methanol is described for example in patent publication WO 2005/095313 A1. A disadvantage here is that the hydrogen-containing gas stream recycled to the methanol synthesis as stream 6 is withdrawn from the pure hydrogen product of the purification unit D and is therefore no longer available for the ammonia synthesis. It would also be desirable to subject further waste streams generated in this process not only to thermal utilization as fuel but rather to material utilization.

SUMMARY

It is accordingly the object of the present invention to specify a process and a plant which does not exhibit the described disadvantages of the prior art and which especially makes it possible in a process for parallel production of methanol and ammonia to achieve preferably material utilization of ideally all material streams generated. The invention shall moreover make it possible to achieve an optimal adjustment of the stoichiometry number for the methanol synthesis without import of hydrogen not produced in the process.

This object is achieved in a first aspect of the invention by a process having the features of claim 1. Further embodiments according to further aspects of the invention are apparent from the subsidiary claims of the respective category.

Synthesis gas production conditions, methanol synthesis conditions, CO conversion conditions, ammonia synthesis conditions are to be understood as meaning the process conditions known per se to a person skilled in the art, in particular of temperature, pressure and residence time, as mentioned for example hereinabove and discussed in detail in the relevant literature and under which at least partial conversion, but preferably industrially relevant conversions of the reactants into the products of the respective process, takes place. The same applies to the choice of a suitable catalysts and suitable operating conditions thereof since in the context of the present invention all recited processes are operated under heterogeneous catalysis with the exception of partial oxidation (POX). Corresponding synthesis gas production reactors, methanol synthesis reactors, CO conversion plants and ammonia synthesis reactors are known per se to those skilled in the art and described for example in the literature described at the outset.

A sorption apparatus in the context of the present disclosure is to be understood as meaning an apparatus which makes it possible for a fluid mixture, for example a gas mixture, to be separated into its constituents or for unwanted components to be separated from the mixture by means of a physical or chemical sorption process using a suitable sorbent. The sorption process may be based on an adsorption, i.e. a bonding of the substance(s) to be separated onto a surface or interface of the solid absorbent, or on an absorption, i.e. a taking-up of the substance(s) to be separated into the volume of the liquid or solid absorbent. The substance(s) separated and bonded by sorption are referred to as adsorbate/absorbate. The bonding forces acting here may be of a physical or chemical type. Accordingly, physical sorption is typically a result of weaker, unspecific bonding forces, for example van der Waals forces, while chemical sorption is a result of stronger, more specific bonding forces and the adsorbate/absorbate and/or the adsorbent/absorbent are chemically altered.

One specific physical absorption process is gas scrubbing with cryogenic methanol which employs methanol having a temperature cooled by refrigerating processes to below ambient temperature, preferably below 0° C., most preferably below −30° C., as the absorbent or scrubbing medium. This process is known to those skilled in the art as the Rectisol process.

In connection with the present invention dividing a material stream is to be understood as meaning splitting of the stream into at least two substreams whose composition of matter and phase state correspond to that of the starting stream. By contrast, separating a material stream is to be understood as meaning splitting of the stream into at least two substreams with the aid of a phase equilibrium, wherein the compositions of the obtained material streams differ from one another and from that of the starting stream.

Liquid nitrogen scrubbing stages are known per se and described for example in Häring, H. W., Industrial Gases Processing, WILEY-VCH Verlag, Weinheim (2008), p. 156. Liquid nitrogen scrubbing stages in the context of the invention are in particular apparatuses in which by means of further cryogenic gas fractionation the obtained offgas stream is separated into a methane-rich gas stream and into a further carbon monoxide- and hydrogen-comprising gas stream which is optionally also employed in international patent application WO 2002/038499 A1.

A main constituent of a material stream is to be understood as meaning components which are present in a proportion of greater than 1% by volume, preferably greater than 10% by volume, and are therefore to be considered as the most important and predominant components of the material stream and substantially define the physicochemical properties of the material stream. By contrast, trace constituents of a material stream are to be understood as meaning components present in a proportion of less than 1% by volume.

The indication that a material stream consists predominantly of one component or group of components is to be understood as meaning that the mole fraction or volume fraction of this component or component group is quantitatively greater than all other proportions of other components or component groups in the material stream each considered alone. Especially in the case of binary mixtures this is to be understood as meaning a proportion of more than 50%. Unless otherwise stated in the specific case, this is based on the volume fraction. In accordance therewith a carbon dioxide-rich stream is to be understood as meaning a material stream where the carbon dioxide proportion is quantitatively greater than all other proportions of other components in the material stream each considered alone and is in particular more than 50% by volume, preferably more than 70% by volume, most preferably more than 90% by volume.

A means is to be understood as meaning something which makes it possible to achieve, or is helpful in achieving, an objective. In particular, means for carrying out a particular process step are all physical objects which a person skilled in the art would take into consideration in order to be able to carry out this process step. For example, a person skilled in the art will consider means of introducing or discharging a material stream to include all transporting and conveying apparatuses, i.e. for example pipelines, pumps, compressors, valves and the corresponding openings in container walls which seem necessary or sensible to said skilled person for performance of this process step on the basis of his knowledge of the art.

Fluid connection between two regions or plant components is to be understood here as meaning any kind of connection that enables flow of a fluid, for example a reaction product or a hydrocarbon fraction, from one to the other of the two regions, irrespective of any interposed regions, components or required conveying means.

All approximate pressures are reported in bar as absolute pressure units, bara for short, or in gauge pressure units, barg for short, unless otherwise stated in the particular individual context.

The invention is based on the finding that it is advantageous in a process for parallel production of methanol and ammonia to achieve preferably material utilization of ideally all material streams generated. This is achieved according to claim 1 by the following measures:

(1) At least a portion of the methanol synthesis purge stream is introduced into the sorption apparatus instead of being thermally utilized as fuel gas for example. The sorption apparatus separates the proportion of carbon dioxide present in the methanol synthesis purge stream. This is preferably carried out together with the converted synthesis gas stream discharged from the CO conversion plant and likewise introduced into the sorption apparatus. This allows further hydrogen to be obtained and supplied to the ammonia synthesis after separation of the deacidified synthesis gas stream discharged from the sorption apparatus in the liquid nitrogen scrubbing stage.

(2) One or more gas streams selected from the group of:
- (2.1) a portion of the converted synthesis gas stream from process step (h)
- (2.2) a portion of the deacidified synthesis gas stream from process step (i)
- (2.3) at least a portion of the second residual gas stream from process step (j2) are introduced into the methanol synthesis reactor.

This makes it possible to establish the stoichiometric $H_2/CO$ ratio of ≥2, for example of 2.1, desired for the methanol synthesis without needing to consume a portion of the pure hydrogen, which is thus entirely at the disposal of the ammonia synthesis, for this purpose.

The measures recited under (1) and (2) moreover interact advantageously since the combination thereof altogether allows provision of more hydrogen at reduced energy cost for the ammonia synthesis on the one hand and for adjusting the stoichiometry number for the methanol synthesis on the other hand. The two partial processes methanol synthesis and ammonia synthesis effect a synergistic interaction that is advantageous and stronger than known from the description of corresponding combined processes in the prior art. However, at the same time, passing a material stream from the methanol synthesis to the ammonia synthesis and passing one or more material streams from the ammonia synthesis to the methanol synthesis or the synthesis gas conditioning arranged upstream of the ammonia synthesis decouples the two partial processes, and fluctuations in one of the partial processes may therefore be compensated to a certain extent by altering these material streams.

In the process according to the invention all of the hydrogen required both for establishing the stoichiometric ratio in the methanol synthesis input gas and in the ammonia synthesis gas may be produced by a CO shift unit. The passing on of a portion of the raw hydrogen, which after the $CO_2$ and methane removal still contains CO, to the methanol synthesis may be utilized for establishing the stoichiometric ratio in the methanol synthesis without the remaining CO being lost to fuel gas, as is the case in hydrogen recovery plants according to the prior art.

The inventive supplying of a hydrogen-rich stream from the liquid nitrogen scrubbing to the methanol synthesis which removes only methane utilizes the unconverted CO in this material stream to the maximum possible extent since this CO participates in the reaction in the methanol synthesis and is thus materially utilized.

Especially the adapting of the stoichiometry number in the methanol synthesis through supply of hydrogen-rich, CO-containing gas, from which in a first scrubbing step of the liquid nitrogen scrubbing only methane has been removed, can be accomplished with very low hydrogen losses. In the same liquid nitrogen scrubbing or in a further separating column a second scrubbing step affords a second, hydrogen-rich gas stream comprising very little, typically <20 ppmv, of CO which is used as an input stream for ammonia synthesis.

It is further advantageous in the process mode according to the invention that a deacidified synthesis gas stream which is freed of carbon dioxide down to the ppm range in the sorption apparatus and additionally dried is obtained from the second raw synthesis gas substream. This has the result that drying and carbon dioxide fine removal apparatuses, which in one example are arranged upstream of the liquid nitrogen scrubbing, may be made smaller.

It is moreover advantageous that the ammonia synthesis feed stream obtained from the liquid nitrogen scrubbing is obtained in cryogenic form and entirely or as a substream may be advantageously utilized in the sorption plant as refrigerant for cooling the converted synthesis gas stream before introduction into the sorption apparatus. This saves the energy for refrigeration and the energy efficiency of the overall process is further improved. The ammonia synthesis feed stream prewarmed in this way is then supplied to the ammonia synthesis.

In a second aspect of the invention the process according to the invention is characterized in that the synthesis gas production plant comprises (b2) an autothermal reforming stage (ATR) or (b3) a partial oxidation stage (POX) or (b4) a combination of the stages (b2) to (b3) with one another or with a steam reforming stage heated using burners and/or hot gases and in that the raw synthesis gas stream produced has a stoichiometry number of less than 2. In these embodiments of the synthesis gas production plant the invention achieves particular advantages since the raw synthesis gas stream produced has a stoichiometry number of less than 2, in one example not more than 1.8, in a further example not more than 1.7. The discussed material utilization of the methanol synthesis purge stream and of the gas stream(s) obtained from the second raw synthesis gas substream and supplied to the methanol synthesis results in particularly effective fashion in an improvement of the hydrogen budget of the overall process. At the same time these embodiments of the synthesis gas production plant provide economic advantages since they are less technically complex and economically costly than, for example, an embodiment with steam reforming. Advantages also arise upon combination of the stages (b2) to (b3) with one another or with a steam reforming stage heated using burners and/or hot gases when the raw synthesis gas stream produced with this combination has a stoichiometry number of less than 2, in one example not more than 1.8, in a further example not more than 1.7.

In a third aspect of the invention the process according to the invention is characterized in that the raw synthesis gas stream produced has a pressure of 40 bara or more, preferably 50 bara or more, most preferably 60 bara or more. What is advantageous here is that the compression effort for the first raw synthesis gas substream, which is passed to the methanol synthesis, and the second raw synthesis gas substream, which is passed to the ammonia synthesis after further conditioning, is significantly reduced. Both are high-pressure synthesis processes; the synthesis pressure in the methanol synthesis is in one example between 50 and 100 bara and the synthesis pressure in the ammonia synthesis is in one example between 250 and 350 bara. Especially the embodiments of the synthesis gas production plant associated with the second aspect of the invention are advantageously employable in connection with the third aspect of the invention, since both autothermal reforming stages and partial oxidation stages are typically operated at elevated pressures markedly above ambient pressure. Typical pressure ranges for autothermal reforming stages are 40 to 60 bara and for partial oxidation stages are 40 to 80 bara.

When implementing the third aspect of the invention the pressure is already elevated in the syngas production part, thus reducing the overall compression energy and also the use of physical $CO_2$ removal techniques.

In a fourth aspect of the invention the process according to the invention is characterized in that the sorption apparatus operates by means of a physical absorption process and in that the sorption apparatus is at the same pressure level as the synthesis gas production plant. Here too, a pressure level of the synthesis gas production plant elevated relative to ambient pressure is advantageous since the solubility of the acidic gas constituent(s) to be separated from the converted synthesis gas stream in the absorbent increases with increasing pressure, thus allowing said constituent(s) to be separated more effectively and with a smaller amount of absorbent.

In a fifth aspect of the invention the process according to the invention is characterized in that the sorption apparatus operates by means of gas scrubbing with cold methanol and in that a carbon dioxide-rich stream having a $CO_2$ content of at least 98% by volume, preferably at least 99% by volume, most preferably at least 99.5% by volume, is discharged from the sorption apparatus. This is a proven physical absorption process featuring high solubility differences between the target components, for example hydrogen and carbon monoxide, and the acidic gas constituents, for example carbon dioxide, as disruptive components, thus making it possible to achieve the recited high $CO_2$ contents at low cost and complexity. An advantage relative to the chemically absorptive scrubbing processes with amines, for example with methyldiethanolamine (MDEA), often used for $CO_2$ removal from ammonia synthesis gas is that the regeneration of the physical scrubbing medium methanol is considerably easier to accomplish, thus reducing the steam consumption for the regeneration and further improving the energy balance of the overall process relative to combined processes known from the prior art. Thus, typical values for required reboiler outputs in scrubbing medium regeneration plants are about 225 MW for amine scrubbing but only about 25 MW for methanol scrubbing (Rectisol process).

In a sixth aspect of the invention the process according to the invention is characterized in that the carbon dioxide-rich stream discharged from the sorption apparatus is sent to a $CO_2$ capture and storage process (CCS) and/or to a process for material utilization of carbon dioxide. The high $CO_2$ contents achievable at low cost and complexity allow for efficient further processing of the acid gas stream since said stream is suitable as a chemical feedstock or for $CO_2$ sequestration for example either immediately or after low-cost fine purification.

In a seventh aspect of the invention the process according to the invention is characterized in that the one or more gas stream(s) introduced into the methanol synthesis reactor are adjusted, based on their molar flow, such that the stoichiometry number of the sum of the feed streams entering the methanol synthesis reactor is at least 2 or more, preferably at least 2.1 or more. It is important when recycling and introducing the hydrogen-containing stream(s) obtained from the converted synthesis gas stream into the methanol synthesis reactor to choose the molar flow(s) such that taking into account all material streams entering the methanol synthesis reactor the stoichiometry number is in the recited range of at least 2 or more, preferably at least 2.1 or more.

In an eighth aspect of the invention the process according to the invention is characterized in that two or more gas streams are simultaneously introduced into the methanol synthesis reactor, wherein the two or more gas streams comprise: (m3) at least a portion of the second residual gas stream from process step (j2) and in addition one or more further gas streams selected from the following group of:

(m1) a portion of the converted synthesis gas stream from process step (h)

(m2) a portion of the deacidified synthesis gas stream from process step (i)

The use of two or more gas streams to adjust the desired stoichiometry number for the methanol synthesis advantageously results in increased flexibility, thus allowing variations or fluctuations in one of the gas streams over time to be compensated by adapting another of the gas streams used. This may be advantageous in non-steady-state plant or process states, for example during bringing online or bringing offline of the process or the plant. As elucidated in connection with the seventh aspect of the invention it is important when recycling and introducing the two or more hydrogen-containing streams into the methanol synthesis reactor to choose the molar flows such that taking into account all material streams entering the methanol synthesis reactor the stoichiometry number is in the recited range of at least 2 or more, preferably at least 2.1 or more.

In a ninth aspect of the invention the plant according to the invention is characterized in that the synthesis gas production plant comprises:

(b2) an autothermal reforming stage (ATR) or (b3) a partial oxidation stage (POX) or (b4) a combination of stages (b2) to (b3)

The technical effect and advantages associated with this aspect correspond to those discussed in connection with the second aspect of the invention.

In a tenth aspect of the invention the plant according to the invention is characterized in that it comprises at least one compression stage which allows the raw synthesis gas stream produced to have a pressure of 40 bara or more, preferably 50 bara or more, most preferably 60 bara or more. The technical effect and advantages associated with this aspect correspond to those discussed in connection with the third aspect of the invention.

In an eleventh aspect of the invention the plant according to the invention is characterized in that the sorption apparatus operates by means of a physical absorption process and is configured such that the sorption apparatus is at the same pressure level as the synthesis gas production plant. The technical effect and advantages associated with this aspect correspond to those discussed in connection with the fourth and fifth aspect of the invention.

In a twelfth aspect of the invention the plant according to the invention is characterized in that the sorption apparatus operates by means of gas scrubbing with cold methanol and is configured such that a carbon dioxide-rich stream having a $CO_2$ content of at least 98% by volume, preferably at least 99% by volume, most preferably at least 99.5% by volume, is discharged from the sorption apparatus. The technical effect and advantages associated with this aspect correspond to those discussed in connection with the fifth aspect of the invention.

In a thirteenth aspect of the invention the plant according to the invention is characterized in that it comprises means which allow the carbon dioxide-rich stream discharged from the sorption apparatus to be sent to a $CO_2$ capture and storage process (CCS) and/or to a process for material utilization of carbon dioxide. The technical effect and advantages associated with this aspect correspond to those discussed in connection with the sixth aspect of the invention.

In a fourteenth aspect of the invention the plant according to the invention is characterized in that it comprises means which allow one or more gas stream(s) introduced into the methanol synthesis reactor to be adjusted, based on their molar flow, such that the stoichiometry number of the sum of the feed streams entering the methanol synthesis reactor is at least 2 or more, preferably at least 2.1 or more. The technical effect and advantages associated with this aspect correspond to those discussed in connection with the seventh aspect of the invention.

BRIEF DESCRIPTION OF THE DRAWINGS

Developments, advantages and possible applications of the invention are also apparent from the following description of working and numerical examples and the drawings. All features described and/or depicted, either in themselves or in any combination, form the invention, regardless of the way they are combined in the claims or the back-references therein.

FIG. 1 shows a schematic representation of the process/the plant according to one embodiment of the invention.

DETAILED DESCRIPTION OF PREFERRED EMBODIMENTS

In the configuration of a process/a plant according to the invention shown in FIG. 1 conduit 12 supplies an input stream containing hydrocarbons, for example natural gas, in a preferred example natural gas having a methane content of at least 80% by volume, to a synthesis gas plant 10 which in this embodiment comprises an autothermal reformer (ATR) and in one example is operated at a pressure of 60 bara.

The synthesis gas production plant 10 carries out an at least partial conversion of the input stream containing hydrocarbons under synthesis gas production conditions to afford a raw synthesis gas stream which contains hydrogen ($H_2$), carbon monoxide (CO) and inert components such as methane ($CH_4$) and is divided into a first raw synthesis gas substream and into a second raw synthesis gas substream.

Via conduit 14 the first raw synthesis gas substream is discharged from the synthesis gas production plant and supplied to a methanol synthesis reactor 20, in which there follows an at least partial conversion of the first raw synthesis gas substream under methanol synthesis conditions. Via conduit 22 a methanol-containing first reactor product stream is discharged from the methanol synthesis reactor 20, cooled to below its dew point and, in a phase separation apparatus not shown separately, separated into a first liquid product stream and a first residual gas stream. The first liquid product stream is sent via conduit 22 as a raw methanol product stream to a methanol workup apparatus 30, which in one example is configured as a distillation, preferably a multistage distillation. A pure methanol stream is discharged from the methanol workup apparatus 30 via conduit 32 and sent for further processing or use.

The first residual gas stream contains unconverted synthesis gas constituents, i.e. hydrogens and carbon oxides, in particular carbon monoxide and carbon dioxide, and inert components, for example methane and/or noble gases, for example argon, unconverted in the synthesis gas production plant. The first residual gas stream is divided into a methanol synthesis purge stream and into a recycle stream, wherein the recycle stream is recycled to the methanol synthesis reactor (not shown separately) and the methanol synthesis purge stream is discharged from the methanol synthesis reactor via conduit 24.

Via conduit 16 the second raw synthesis gas substream is discharged from the synthesis gas production plant and introduced into a CO conversion plant 40 which comprises at least one CO conversion stage. Carried out in the CO conversion stage by addition of steam (not shown separately) is a conversion of the carbon monoxide present in the second raw synthesis gas substream under CO conversion conditions into a converted synthesis gas stream having a content of hydrogen and carbon dioxide which has been elevated relative to the second raw synthesis gas substream. The converted synthesis gas stream is discharged from the CO conversion plant 40 via conduit 42.

The converted synthesis gas stream is introduced via conduit 42 into a sorption apparatus 50 for removal of acidic gas constituents, especially carbon dioxide, by means of a physical or chemical sorption process. In one example the sorption apparatus 50 is configured for performing a gas scrubbing with the physical absorbent methanol (Rectisol process). This affords a deacidified synthesis gas stream which is discharged from the sorption apparatus 50 via conduit 52. Also obtained is an acid gas stream containing acidic gas constituents which is discharged via conduit 54. In one example the sorption apparatus 50 is configured and operated such that conduit 54 discharges from the sorption apparatus a dry, carbon dioxide-rich stream having a $CO_2$ content of at least 90% by volume, preferably at least 99% by volume, most preferably at least 99.5% by volume. This makes it possible for the carbon dioxide-rich stream discharged from the sorption apparatus to be supplied to a $CO_2$ capture and storage process (CCS) and/or to a process for material utilization of carbon dioxide directly, i.e. without a further conditioning or purification step.

The deacidified synthesis gas stream is introduced into a liquid nitrogen scrubbing stage 60 via conduit 52. In one example the deacidified synthesis gas stream is, prior to sending to liquid nitrogen scrubbing stage 60, supplied to one or more drying and carbon dioxide fine removal apparatuses (not shown separately) to remove traces of water and/or carbon dioxide which would otherwise freeze out in the liquid nitrogen scrubbing stage and can lead to blockages therein. It is advantageous that a deacidified synthesis gas stream which is freed of carbon dioxide down to the ppm range in the sorption apparatus and additionally dried is obtained from the second raw synthesis gas substream. This has the result that drying and carbon dioxide fine removal apparatuses, which in this example are arranged upstream of the liquid nitrogen scrubbing, may be made smaller.

The liquid nitrogen scrubbing stage 60 effects separation, for example multistage separation, of the deacidified synthesis gas stream in the liquid nitrogen scrubbing stage 60 into the following substreams:

(60.1) an ammonia synthesis feed stream containing hydrogen and nitrogen as main constituents and carbon monoxide and inert components as trace constituents, (60.2) a second residual gas stream containing hydrogen and carbon monoxide as main constituents and inert components as trace constituents, (60.3) an inert gas stream which contains inert components as the main constituent and is discharged from the process.

The obtained material stream (60.1) is introduced via conduit 62 into an ammonia synthesis reactor 70 as the ammonia synthesis feed stream. Appropriate configuration of the liquid nitrogen scrubbing stage 60/the operation thereof ensures that the trace proportions of carbon monoxide and inert components present in the ammonia synthesis feed stream do not adversely affect the subsequent ammonia synthesis. It is further ensured that the ammonia synthesis feed stream contains a hydrogen/nitrogen mixture of desired composition, for example having a molar hydrogen/nitrogen ratio of 3 according to the stoichiometry of the ammonia synthesis reaction.

The obtained material stream (60.3) which contains inert components, in particular methane, as the main constituent is used as fuel gas for example on account of its calorific value after discharging from the process. It may alternatively be recycled to the synthesis gas production plant 10 as part of the input stream containing hydrocarbons. If the stream (60.3) contains significant proportions of components such as for example argon, which cannot be converted in the synthesis gas production plant, it is advisable to recycle only a portion of the stream (60.3) to the synthesis gas production plant to avoid accumulation of these substances.

The ammonia synthesis reactor 70 carries out an at least partial conversion of the ammonia synthesis feed stream under ammonia synthesis conditions. An ammonia product stream is then discharged from the ammonia synthesis reactor 70 via conduit 72 and sent for further use or processing.

According to the invention at least a portion of the methanol synthesis purge stream is introduced into the sorption apparatus 50 via conduit 24. The introducing may be effected directly into the sorption apparatus and/or into the conduit 42 which opens into the sorption apparatus. The sorption apparatus also separates the carbon dioxide proportion from the methanol synthesis purge stream, thus making the remaining proportions of carbon monoxide and hydrogen more amenable for utilization in the subsequent process steps/plant parts.

Furthermore, according to the invention the second residual gas stream (60.2) containing hydrogen and carbon monoxide as main constituents is recycled to the methanol synthesis reactor 20 via conduit 64, thus allowing material utilization of these main constituents in the methanol synthesis. Alternatively or in addition a portion of the converted synthesis gas stream from the CO conversion stage or downstream thereof and/or portion of the deacidified synthesis gas stream from the sorption apparatus or downstream thereof may be recycled to the methanol synthesis reactor 20 (not shown separately in both cases). Mixtures of these three potential recycle streams are also possible to provide even greater flexibility in terms of the establishment of recycling streams to the methanol synthesis reactor.

The recycling of one or more of the recited material streams allows material utilization of the proportions of hydrogen and carbon monoxide present therein in the methanol synthesis reactor for production of additional methanol. This also allows the desired stoichiometry number in the methanol synthesis reactor to be established without the need to import hydrogen from outside the process or to withdraw hydrogen from a pure hydrogen stream. Such a pure hydrogen stream is in any case not readily available within the process according to the invention since the stream (60.1) already contains a stoichiometric proportion of nitrogen. In the context of the methanol synthesis nitrogen is an inert component and therefore unwanted therein.

Increasing the pressure in the synthesis gas production plant to 60 bara has a positive effect on the overall economy of the process since it contributes to a reduction in the compression energy required for the methanol synthesis. Furthermore, the pressure increase also results in an improved absorption of carbon dioxide in the physical scrubbing medium methanol in relation to lower pressures in the sorption apparatus configured according to the Rectisol process.

The passing on of purge gas from the methanol synthesis reactor to the $CO_2$ removal in the sorption apparatus and subsequently to the cryogenic removal of methane and the subsequent passing on of the purified raw hydrogen and the CO proportion remaining therein for the methanol synthesis improve the efficiency of the overall process without any need for additional purification apparatuses such as a pressure swing adsorption (PSA) or membrane plants.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

LIST OF REFERENCE SYMBOLS

10 Synthesis gas production plant
12 Conduit
14 Conduit
16 Conduit
20 Methanol synthesis reactor
22 Conduit
24 Conduit
30 Methanol workup apparatus (methanol distillation)
40 CO conversion plant
42 Conduit
50 Sorption apparatus (Rectisol)
52 Conduit
54 Conduit
60 Liquid nitrogen scrubbing stage
62 Conduit
64 Conduit
70 Ammonia synthesis reactor
72 Conduit

What is claimed is:

1. A process for producing methanol and ammonia from an input stream comprising hydrocarbons, comprising:

(a) providing an input stream containing hydrocarbons, (b) supplying the input stream containing hydrocarbons to a synthesis gas production plant comprising, (b1) a steam reforming stage heated using burners and/or hot gases or (b2) an autothermal reforming stage or (b3) a partial oxidation stage or (b4) a combination of at least two of the stages (b1) to (b3), (c) at least partially converting the input stream containing hydrocarbons in the synthesis gas production plant under synthesis gas production conditions thereby producing a raw synthesis gas stream containing hydrogen, carbon monoxide and inert components, (d) discharging the raw synthesis gas stream from the synthesis gas production plant and dividing the raw synthesis gas stream into a first raw synthesis gas substream and into a second raw synthesis gas substream, (e) introducing at least a portion of the first raw synthesis gas substream into a methanol synthesis reactor, at least partially converting the first raw synthesis gas substream in the methanol synthesis reactor under methanol synthesis conditions, thereby producing a methanol-containing first reactor product stream, (f) discharging the methanol-containing first reactor product stream from the methanol synthesis reactor, cooling the first reactor product stream to below its dew point and separating the cooled first reactor product stream in a phase separation apparatus into a first liquid product stream and a first residual gas stream containing unconverted synthesis gas constituents and inert components, discharging the first liquid product stream from the process as a raw methanol product stream, (g) dividing the first residual gas stream into a methanol synthesis purge stream and into a recycle stream which is recycled to the methanol synthesis reactor, (h) introducing at least a portion of the second raw synthesis gas substream into a carbon monoxide conversion plant comprising at least one carbon monoxide conversion stage, converting the portion of the second raw synthesis gas substream introduced into the carbon monoxide conversion plant under carbon monoxide conversion conditions to afford a converted synthesis gas stream, discharging the converted synthesis gas stream, (i) introducing the converted synthesis gas stream into a sorption apparatus for removal of acidic gas constituents by means of a physical or chemical sorption process, discharging a deacidified synthesis gas stream and an acid gas stream containing acidic gas constituents from the sorption apparatus, discharging the acid gas stream from the process, (j) introducing at least a portion of the deacidified synthesis gas stream into a liquid nitrogen scrubbing stage, separating the deacidified synthesis gas stream in the liquid nitrogen scrubbing stage into the following substreams:

(j1) an ammonia synthesis feed stream containing hydrogen and nitrogen as main constituents and carbon monoxide and inert components as trace constituents, (j2) a second residual gas stream containing hydrogen and carbon monoxide as main constituents and inert components as trace constituents, (j3) an inert gas stream which contains inert components as the main constituent and is discharged from the process, (k) introducing the ammonia synthesis feed stream into an ammonia synthesis reactor, at least partially converting the ammonia synthesis feed stream in the ammonia synthesis reactor under ammonia synthesis conditions, discharging an ammonia product stream from the ammonia synthesis reactor, (l) introducing at least a portion of the methanol synthesis purge stream into the sorption apparatus, (m) introducing into the methanol synthesis reactor one or more gas streams selected from the following group of:

(m1) a portion of the converted synthesis gas stream from process step (h)

(m2) a portion of the deacidified synthesis gas stream from process step (i)

(m3) at least a portion of the second residual gas stream from process step (j2).

2. The process according to claim 1, wherein the synthesis gas production plant comprises:

(b2) an autothermal reforming stage or (b3) a partial oxidation stage or (b4) a combination of the stages (b2) to (b3) with one another or with a steam reforming stage heated using burners and/or hot gases and in that the raw synthesis gas stream produced has a stoichiometry number of less than 2.

3. The process according to claim 2, wherein the raw synthesis gas stream produced has a pressure of 40 bara or more.

4. The process according to claim 3, wherein the sorption apparatus operates by means of a physical absorption process and in that the sorption apparatus is at the same pressure level as the synthesis gas production plant.

5. The process according to claim 1, wherein the one or more gas stream(s) introduced into the methanol synthesis reactor are adjusted, based on their molar flow, such that the stoichiometry number of the sum of the feed streams entering the methanol synthesis reactor is at least 2 or more.

6. The process according to claim 1, wherein two or more gas streams are simultaneously introduced into the methanol synthesis reactor, wherein the two or more gas streams comprise: (m3) at least a portion of the second residual gas stream from process step (j2) and in addition one or more further gas streams selected from the following group of:

(m1) a portion of the converted synthesis gas stream from process step (h)

(m2) a portion of the deacidified synthesis gas stream from process step (i).

* * * * *